United States Patent
McKenna

(10) Patent No.: US 8,859,631 B2
(45) Date of Patent: Oct. 14, 2014

(54) TWO STAGE PROCESS FOR THE CONVERSION OF SYNTHESIS GAS USING A COBALT CATALYST IN THE FIRST STAGE AND A SUPPORTED RUTHENIUM CATALYST IN THE SECOND STAGE

(75) Inventor: Mark McKenna, Stockton on Tees (GB)

(73) Assignee: Johnson Matthey PLC, London (GB)

( * ) Notice: Subject to any disclaimer, the term of this patent is extended or adjusted under 35 U.S.C. 154(b) by 213 days.

(21) Appl. No.: 13/521,923

(22) PCT Filed: Dec. 16, 2010

(86) PCT No.: PCT/GB2010/052116
§ 371 (c)(1),
(2), (4) Date: Jan. 4, 2013

(87) PCT Pub. No.: WO2011/089377
PCT Pub. Date: Jul. 28, 2011

(65) Prior Publication Data
US 2013/0116349 A1 May 9, 2013

(30) Foreign Application Priority Data
Jan. 21, 2010 (GB) .................................. 1000971.0

(51) Int. Cl.
*C07C 27/00* (2006.01)
*C10G 2/00* (2006.01)
*C07C 1/04* (2006.01)

(52) U.S. Cl.
CPC .............. *C07C 1/0485* (2013.01); *C10G 2/333* (2013.01); *C10G 2300/4081* (2013.01); *C10G 2/332* (2013.01)
USPC ............ 518/706; 518/700; 518/705; 518/715

(58) Field of Classification Search
CPC .................. C10G 2/332; C10G 2/333; C10G 2300/4081; C07C 1/0485
USPC ................... 518/700, 705, 706, 715
See application file for complete search history.

(56) References Cited

U.S. PATENT DOCUMENTS

| 4,624,968 | A | 11/1986 | Kim et al. |
| 5,028,634 | A | 7/1991 | Fiato |
| 2002/0151605 | A1 | 10/2002 | Kibby |
| 2002/0187094 | A1 | 12/2002 | Motal et al. |

OTHER PUBLICATIONS

Rawle et al., "Basic Principles of Particle Size Analysis," Technical Paper No. MRK034, Malvern Instruments Limited, 2001, pp. 1-8.
International Search Report dated Nov. 7, 2001, from PCT International Application No. PCT/GB2010/052116.
International Preliminary Report on Patentability dated Jul. 24, 2012, from PCT International Application No. PCT/GB2010/052116.

*Primary Examiner* — Jafar Parsa
(74) *Attorney, Agent, or Firm* — RatnerPrestia

(57) ABSTRACT

A process is described for the conversion of synthesis gas into hydrocarbons including the steps of;
(i) passing a synthesis gas comprising hydrogen and carbon monoxide over a cobalt catalyst at elevated temperature and pressure to produce a first reaction product mixture comprising hydrocarbons, steam, carbon monoxide and hydrogen,
(ii) condensing and separating water from the first reaction product mixture to produce a de-watered first reaction product mixture,
(iii) passing the de-watered first reaction product mixture over a supported ruthenium catalyst at elevated temperature and pressure to produce a second reaction product mixture containing hydrocarbons, and
(iv) recovering the hydrocarbons from the second reaction product mixture.

27 Claims, 1 Drawing Sheet

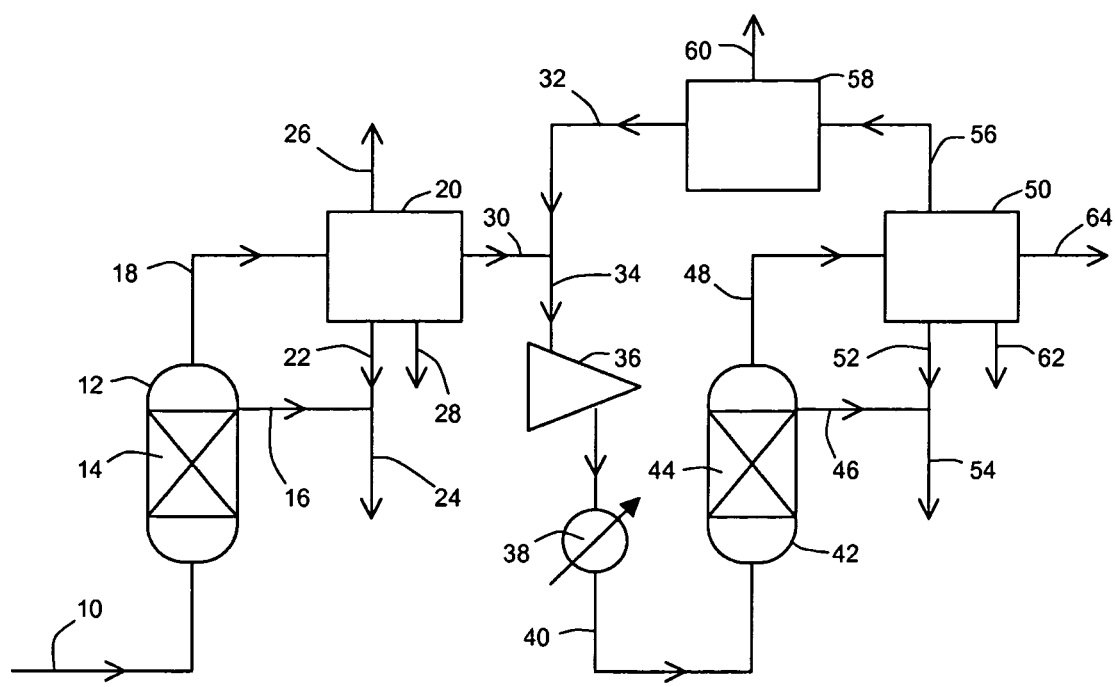

TWO STAGE PROCESS FOR THE CONVERSION OF SYNTHESIS GAS USING A COBALT CATALYST IN THE FIRST STAGE AND A SUPPORTED RUTHENIUM CATALYST IN THE SECOND STAGE

CROSS-REFERENCE TO RELATED APPLICATIONS

This application is the U.S. National Phase application of PCT International Application No. PCT/GB2010/052116, filed Dec. 16, 2010, and claims priority of British Patent Application No. 1000971.0, filed Jan. 21, 2010, the disclosures of both of which are incorporated herein by reference in their entireties for all purposes.

FIELD OF THE INVENTION

This invention relates to a process for the conversion of synthesis gas into hydrocarbons including the Fischer-Tropsch synthesis of hydrocarbons.

Synthesis gas is a term usually given to a mixture of hydrogen and carbon oxides, although other components such as methane and inert gases (nitrogen and/or argon) may also be present depending upon the feedstock and synthesis gas generation process. The conversion of synthesis gases derived from various sources into useful chemicals is growing in importance. In particular, synthesis gases derived by steam reforming or partial oxidation of natural gas and naphtha, or from the gasification of coal, petroleum tars, or biomass, may usefully be turned into liquid hydrocarbon fuels, lubricants, and chemical feedstocks, such as methanol, dimethylether, and alpha-olefins.

Conversion of synthesis gases comprising hydrogen and carbon monoxide by the Fischer-Tropsch synthesis of hydrocarbons has received much attention. In this process a synthesis gas mixture comprising principally of hydrogen and carbon monoxide at a molar ratio generally in the range 1.6:1-3.0:1 is passed at elevated temperature and pressure over cobalt or iron catalysts. The Fischer-Tropsch process involves a variety of competing reactions, which lead to a series of desirable products and undesirable by-products. When using cobalt catalysts, the most important reactions are those resulting in the formation of alkanes with co-produced water as a by-product. This reaction may be depicted as follows;

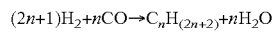

$(2n+1)H_2 + nCO \rightarrow C_nH_{(2n+2)} + nH_2O$ where n is a positive integer. Since methane (n=1) is mostly considered an unwanted by-product, process conditions and catalyst composition are usually chosen to favour higher molecular weight (n>1) products, especially where n≥5. In addition to alkane formation, competing reactions result in the formation of alkenes, as well as alcohols and other oxygenates. Typically, cobalt-catalysed processes are operated to minimise alkene and oxygenate formation although iron catalysts have been used to generate alkene-rich streams. Ruthenium catalysts are also known to be effective in alkane synthesis, but are not used commercially because of their higher relative costs and modest reactivity. Cobalt catalysts are preferred because they operate at lower temperatures than iron catalysts and can produce product streams rich in higher hydrocarbons suitable for processing into synthetic fuels.

Synthesis gases often contain sulphur compounds, such as hydrogen sulphide and other catalyst poisons, and while measures may be taken to reduce them, deactivation of the cobalt catalysts still occurs leading to a requirement to replace spent catalyst at regular intervals. Current commercial cobalt catalysts generally contain one or more promoter metals, such as rhenium or platinum, that enhance the performance of the catalyst but render recycling of the spent catalyst difficult and expensive.

SUMMARY OF THE INVENTION

The present invention provides a process where a sacrificial, recyclable cobalt catalyst is used to efficiently convert a portion of the synthesis gas and trap catalyst poisons, and a ruthenium catalyst is used to convert the remaining portion of the synthesis gas in a second stage. In addition, the overall selectivity of the process using such a catalyst combination is surprisingly significantly enhanced Accordingly the invention provides a process for the conversion of synthesis gas into hydrocarbons comprising the steps of;

(i) passing a synthesis gas comprising hydrogen and carbon monoxide over a cobalt catalyst at elevated temperature and pressure to produce a first reaction product mixture comprising hydrocarbons, steam, carbon monoxide, and hydrogen, (ii) condensing and separating water from the first reaction product mixture to produce a de-watered first reaction product mixture, (iii) passing the de-watered first reaction product mixture over a supported ruthenium catalyst at elevated temperature and pressure to produce a second reaction product mixture containing hydrocarbons, and (iv) recovering the hydrocarbons from the second reaction product mixture.

It will be understood that the cobalt and ruthenium catalysts are not mixed and preferably are in separate reaction vessels.

BRIEF DESCRIPTION OF THE DRAWING

The process will now be further described by reference to the attached drawing, in which;

FIG. 1 depicts a flowsheet according to one embodiment of the present invention.

DETAILED DESCRIPTION OF THE INVENTION

A synthesis gas having a hydrogen:carbon monoxide ratio in the range 1.6:1-3.0:1, preferably 1.7:1-2.5:1 may be used. The synthesis gas may be generated by steam reforming and/or partial oxidation of natural gas and naphtha, or from the gasification of coal, petroleum tars, or biomass.

The process is preferably operated such that a minor portion of the synthesis gas is converted to hydrocarbons over the cobalt catalyst and a major portion is converted over the ruthenium catalyst.

The benefits of the process include (1) the first stage cobalt catalyst acting as a so-called "guard" for the second stage ruthenium catalyst, removing any species in the synthesis gas that are poisonous to the desired hydrocarbon synthesis reactions, (2) the ability to operate at high hydrogen partial pressures over the cobalt catalyst to maximize activity while minimizing oxidative deactivation of the active metallic cobalt from co-produced water, and (3) allowing a lower reaction temperature, thereby enhancing selectivity to C5+ hydrocarbons. Furthermore, the invention allows simple non-promoted cobalt catalyst formulations to be used minimizing the cost and enhancing the recyclablility of the spent catalysts. We have found that the efficiency of the ruthenium catalyst is surprisingly enhanced, particularly by operation at higher pressure and temperature on the partially converted synthesis gas, which allows higher-grade steam generation, while maintaining the overall process selectivity to C5+ hydrocarbons at a higher level than a cobalt-only catalysed process.

The cobalt catalyst may comprise cobalt supported on an oxidic support or silicon carbide support. Such catalysts are commercially available and are typically produced by impregnation of the support with a suitable cobalt salt solution, followed by drying, calcination to convert the cobalt compounds to cobalt oxide, followed usually by a reduction step in which the cobalt oxide is reduced to its active, elemental form. Powder supports may be used to generate powder catalysts. Alternatively, where the support is a powder, the catalyst may, if desired, be shaped before or after impregnation or calcination to generate a shaped catalyst precursor, which is then reduced. Suitable cobalt salts include cobalt nitrate, cobalt acetate and cobalt ammine carbonate. The oxidic support may be selected from alumina, silica, titania, zirconia, zinc oxide, or a mixture thereof. Preferred catalysts for use in the present invention comprise an alumina support, such as an alpha alumina, a transition alumina, a hydrated alumina, or an alpha alumina or transition alumina coated in a layer of metal aluminate. Gamma, delta, and theta aluminas, and mixtures thereof, and metal aluminates, such as lithium, cobalt, or nickel aluminate, are particularly suitable cobalt catalyst supports.

Alternatively, the cobalt catalyst may comprise an intimate mixture of cobalt and oxidic compounds. Such intimate mixtures may be formed by the co-precipitation or sequential precipitation of cobalt and oxidic, hydroxy-, carbonate-, or hydroxycarbonate compounds from solution, followed by washing, drying, calcining, and reduction/encapsulation. Preferred catalysts of this type comprise cobalt and cobalt-aluminium oxide or cobalt-zinc oxide compounds.

Alternatively, the cobalt catalyst may be formed by a deposition-precipitation method in which an ammine-cobalt complex, e.g. a cobalt ammine carbonate, is heated in the presence of a powder or shaped catalyst support to decompose the complex and deposit cobalt compounds, which may be directly reduced or calcined and reduced to form the active catalyst.

The cobalt catalyst may further comprise one or more oxidic or precious metal promoters known in the art to enhance the catalyst stability. In a preferred embodiment however, the cobalt catalyst is free of precious metal promoters, i.e., the cobalt catalyst consists essentially of cobalt or cobalt compounds and a support material.

Desirably, the cobalt content of the cobalt catalyst is in the range 5-45% by weight, preferably 15-35% by weight, more preferably 20-30% by weight.

The cobalt catalyst may be in the form of powders or shaped units, such as pellets, extrudates or granules, depending upon the first stage reactor technology chosen. Pellets, extrudates, or granules, which may be used in fixed bed arrangements, typically have a particle size, usually expressed as the width or diameter, in the range 1 to 25 mm and an aspect ratio (i.e. length/width) of <10. For example 1-10 mm diameter extrudates, such as trilobal extrudates, may suitably be used in fixed bed reactor configurations. Catalyst powders, which may comprise agglomerates formed by spray drying, having an average particle size, expressed as volume-median diameter $D[v,0.5]$, in the range of 1 to 200 micrometers, may suitably be used in slurry-phase reactor configurations. In certain applications, it is advantageous to use particles which have a volume-median diameter $D[v,0.5]$, in the range from 25-150 μm. For other applications, e.g. as a catalyst for reactions carried out in a fluidised bed, it may be desirable to use larger particle sizes, preferably with $D[v,0.5]$ in the range 25 to 1000 μm or larger. The term volume-median diameter $D[v,0.5]$, sometimes given as $D_{50}$ or $D_{0.5}$, is defined by Dr. Alan Rawle in the paper "Basic Principles of Particle Size Analysis" available from Malvern Instruments Ltd, Malvern, UK (see www.malvern.co.uk), and is calculated from the particle size analysis which may conveniently be effected by laser diffraction for example using a "Malvern Mastersizer.".

Alternatively, the catalyst may be provided as a coating on a metal or ceramic support, such as a monolith or foam structure, using known wash-coating techniques.

The ruthenium catalyst preferably comprises ruthenium supported on a support such as an oxidic support or silicon carbide support. Graphite may also be used as a support. These catalysts are typically prepared by an impregnation method analogous to the cobalt catalysts described above, and the supports therefore are desirably selected from alumina, silica, titania, zirconia, zinc oxide, or a mixture thereof. Alumina-containing supports are preferred. The alumina-containing support may be an alpha alumina, a transition alumina, such as a gamma-, delta-, or theta-alumina, a hydrated alumina or a metal aluminate, such as lithium aluminate or an alumina coated in a layer of metal aluminate. Transition aluminas, alpha alumina and metal-aluminate supports, such as lithium aluminate, or metal-aluminate-coated alumina supports, are particularly preferred.

While the ruthenium catalyst may contain other catalytically active precious metals, such as platinum or rhenium, desirably the ruthenium catalyst is free of cobalt, i.e. the ruthenium catalysts preferably consists essentially of ruthenium or ruthenium compounds and a support material. The ruthenium content of the ruthenium catalyst may be in the range 0.1-10% by weight, preferably 0.5-7.5% by weight, more preferably 1-7.5% by weight, most preferably 2.5-7.5% by weight.

Like the cobalt catalyst, the ruthenium catalyst may be in the form of powders or shaped units, such as pellets, extrudates or granules, depending upon the second stage reactor technology chosen. For example 1-10 mm extrudates, e.g. trilobal extrudates, may suitably be used in fixed bed reactor configurations, whereas 1-200 micrometer powders, which may comprise agglomerates formed by spray drying, may suitably be used in slurry-phase reactor configurations. Alternatively, the Ru catalyst may be provided as a coating on a metal or ceramic support, such as a monolith or foam structure, using known wash-coating techniques.

The cobalt and ruthenium catalysts may be provided in oxidic form and reduced in-situ, but are more commonly provided to the reactors reduced and encapsulated in a suitable protective coating, such as a hydrocarbon wax.

The operating conditions of the process may be suitably controlled to achieve the desired range of products. The process may be operated at pressures in the range 0.1-10 MPa and temperatures in the range 150-350° C. Preferably, the first reaction stage to produce the first reaction product mixture is operated at a temperature in the range 210-225° C. and a pressure in the range 5-60 bar abs, preferably 10-30 bar abs, more preferably 18-24 bar abs, especially 20-22 bar abs. The second reaction stage to produce the second reaction product mixture may be operated at a temperature in the range 230-265° C., preferably in the range 250-265° C., and a pressure in the range 30-60 bar abs, preferably 35-55 bar abs, more preferably 40-50 bar abs. In a preferred embodiment, the operating pressure of the second reaction stage is higher than that of the first reaction stage as this takes advantage of the activity of the ruthenium catalyst to complete the conversion of the hydrogen depleted synthesis gas at relatively higher water partial pressures than cobalt catalysts. The pressure may suitably be increased by one or more stages of compression of the first stage reaction product.

The first reaction stage may be performed by passing the synthesis gas mixture through a fixed bed of the cobalt catalyst or through a slurry of the cobalt catalyst in a hydrocarbon liquid medium. Any known fixed bed or slurry phase reactor technology may be used, for example single or multiple bed, cooled heat exchange fixed bed reactors, stirred slurry-phase reactors, jet-loop reactors, bubble-column reactors, or fluidised bed reactors. The second reaction stage may also be performed by passing the synthesis gas mixture through a fixed bed of the ruthenium catalyst or, preferably, through a slurry of the ruthenium catalyst in a hydrocarbon liquid medium in a suitable slurry-phase reactor.

The gas-hourly-space velocity (GHSV) for continuous operation may be in the range 100-25000 $hr^{-1}$. A preferred operating range is typically 1000-15000 $hr^{-1}$.

In order to improve the efficiency of the process, it is desirable to adjust the temperature and/or pressure of the first reaction product mixture, such that water condenses from the mixture. The condensate may then be recovered from the first reaction product mixture using conventional separation equipment before feeding the resulting de-watered first reaction product mixture to the second stage catalyst.

Liquid and gaseous hydrocarbons may also be separated from the first reaction product mixture at this time. The recovery of hydrocarbons from the second stage reaction product mixture may be achieved using conventional methods, such as cooling, separation, and distillation.

In order to achieve the desired conversion, whether or not there is any compression of the de-watered first reaction product gas mixture, the temperature of the de-watered first reaction product gas mixture may be adjusted by heat exchange before the second reaction stage. This may be achieved for example using a conventional steam heater utilizing high pressure steam derived from the heat recovery from the raw synthesis gas. If desired, the composition of the first stage reaction mixture, before or after water removal, may be adjusted by addition of one or more of synthesis gas, hydrogen, carbon monoxide, or an inert gas, or by the removal of hydrocarbon and/or steam. However this may not be necessary where the $H_2$:CO stoichiometry of the feed synthesis gas is >2:1.

In a preferred embodiment, the process is operated, such that >50%, preferably >60%, more preferably >70% of the conversion of the synthesis gas occurs over the ruthenium catalyst. Thus, the cobalt catalyst effects conversion of a minor portion of the synthesis gas fed to the process. By using a combination of cobalt and ruthenium catalysts, the process of the present invention may be operated such that the conversion of the synthesis gas to hydrocarbons in the second stage reaction mixture is ≥90%, preferably ≥95%, on a molar basis. This reduces the volume of recycle gases, compared to cobalt-only catalysed Fischer-Tropsch processes.

The recovery of hydrocarbons from the second stage reaction product mixture may be achieved using conventional methods, such as cooling, separation, and distillation. Such recovery may create a tail gas comprising hydrogen, carbon monoxide, carbon dioxide, and methane, which may be utilized further. Thus, if desired, at least a portion of the tail gas may be recycled to one or more of an upstream synthesis gas generation stage, the synthesis gas fed to the cobalt catalyst, the first stage reaction product mixture fed to the ruthenium catalyst, or a separation stage that provides one or more gases enriched in hydrogen, carbon monoxide, carbon dioxide, or methane. If desired, at least a portion of the gases enriched in hydrogen, carbon monoxide, carbon dioxide, or methane may be recycled to one or more of an upstream synthesis gas generation stage, the synthesis gas fed to the cobalt catalyst, the first stage reaction product mixture fed to the ruthenium catalyst, or a downstream hydrocarbon processing stage. In a preferred embodiment, $CO_2$ formed in the first and second stages is recovered from the tail gas and fed to an upstream synthesis gas generation stage or is compressed and sent for storage and/or used in enhanced oil recovery processes. The resulting $CO_2$-depleted tail gas, comprising hydrogen and carbon monoxide, may be fed to one or more of the synthesis gas fed to the cobalt catalyst, the first stage reaction product mixture fed to the ruthenium catalyst, or a downstream hydrocarbon processing stage.

In a preferred embodiment, after recovery of the hydrocarbons and separation of the co-produced water, at least a portion of the tail gas or the gas enriched in hydrogen, carbon monoxide, or methane from any separation stage, is recycled to the feed to the second stage, i.e. recycled to the ruthenium-catalysed stage. The high selectivity of the ruthenium catalyst allows for the efficient recycle of tail gas to the second reaction stage compared to cobalt-only catalysed processes. The portion of tail gas not recycled to the hydrocarbon synthesis, which may be termed the "tail gas purge stream," is at elevated pressure and so may usefully be passed through a turbo expander to generate power before being used, e.g. as a fuel.

The recovery of hydrocarbons from the first and second stage reaction product mixture generally creates a co-produced water stream comprising water and oxygenated hydrocarbons. If desired, at least a portion and preferably >50% vol, more preferably >75% vol, of the co-produced water may be recycled to an upstream synthesis gas generation stage and/or a separation stage that provides a stream enriched in oxygenates. At least a portion of the oxygenates from any separation stage may be recycled to an upstream synthesis gas generation stage. By recycling the oxygenates in this way, the carbon-efficiency of the process is enhanced while at the same time need for sophisticated water treatment is reduced.

The crude mixture of hydrocarbons recovered from the process may be further refined to generate synthetic fuels, lubricants or chemicals using conventional methods.

In FIG. 1 a synthesis gas mixture comprising $H_2$ and CO at a molar ratio of about 2:1, at a temperature in the range 210-220° C. and a pressure of about 20 bar abs is fed via line 10 to a slurry phase reactor 12 containing a slurry 14 of a cobalt catalyst consisting of 20-25% wt. cobalt on a transition alumina powder catalyst suspended in a molten hydrocarbon wax. The hydrogen and carbon monoxide react in the presence of the cobalt catalyst to form a crude first stage reaction product mixture comprising liquid hydrocarbons, gaseous hydrocarbons, and steam, as well as unreacted hydrogen and carbon monoxide and some formed carbon dioxide. The feed to the reactor 12 is controlled, such that the conversion of the synthesis gas to hydrocarbons over the cobalt catalyst is about 30%. Liquid hydrocarbons are recovered from the reactor 12 via line 16. The gaseous products mixture is fed from the reactor via line 18 to a first separation unit 20 that condenses water and hydrocarbons and separates them from the gaseous components by means of one or more stages of separation and distillation. The condensed liquid hydrocarbons are recovered from the unit 20 via line 22 and combined with the liquid hydrocarbon product stream 16 to provide a liquid hydrocarbon product stream 24, which may also be termed a FT wax stream. The gaseous hydrocarbon components are recovered from the separation unit 20 via line 26. The condensed water is recovered from the separation unit 20 via line 28. The de-watered first stage reaction product mixture 30 comprising hydrogen and carbon monoxide is then mixed with a recycle stream 32 and fed via line 34 to compressor 36 where it is compressed to a pressure in the range 40-50 bar abs. The temperature of the compressed mixture is then adjusted to 210-250° C. by means of heat exchanger 38. The compressed, temperature-adjusted gas mixture is then fed from heat exchanger 38 via line 40 to a second reactor 42 containing a slurry 44 of a catalyst consisting of ca. 5% wt. ruthenium on alpha alumina powder suspended in a molten hydrocarbon wax. The remaining hydrogen and carbon monoxide react in the presence of the ruthenium catalyst to form a crude second stage reaction product mixture comprising liquid hydrocarbons, gaseous hydrocarbons, and steam. The feed to the reactor 42 is controlled, such that the overall conversion of the synthesis gas to hydrocarbons in the process is >90%. Liquid hydrocarbons are recovered from the reactor 42 via line 46. The gaseous product mixture is fed from the reactor 42 via line 48 to a second separation unit 50 that condenses water and hydrocarbons and separates them from the gaseous components by means of one or more stages of separation and distillation. The condensed liquid hydrocarbons are recovered from the unit 50 via line 52 and combined with the liquid hydrocarbon product stream 46 to provide a liquid hydrocarbon product stream 54. If desired this stream may be combined with liquid hydrocarbon product stream 24 (not shown). A tail gas is recovered from the separation unit 50 and a first portion is fed via line 56 to a third separation unit 58 comprising a membrane that separates a $CO_2$ stream 60 from the tail gas. The $CO_2$ stream may be fed to the synthesis gas generation stage or compressed and sent for storage and/or used in enhanced oil recovery processes. The $CO_2$-depleted tail gas is fed from separation unit 58 via line 32 to be combined with the de-watered first stage reaction product gas in line 30. A second portion of the tail gas is recovered from the separation unit 50 as a tail gas purge stream 64. This tail gas purge stream may be passed through a turbo expander to generate power and/or used as fuel or as a source of hydrogen for upstream or downstream processes. The condensed water is recovered from the separation unit 50 via line 62.

The co-produced water 28, 62 may be further processed to remove oxygenates and the oxygenates, or the co-produced water, recycled upstream to the synthesis gas generation stage (not shown).

EXAMPLE

The invention is further illustrated by reference to the following calculated example based on the flowsheet depicted in FIG. 1 utilizing laboratory-generated activity and selectivity data for the catalysts.

| | | Stream Number | | | | | |
|---|---|---|---|---|---|---|---|
| | | 10 | 18 | 26 | 16 | 22 | 24 |
| Temperature | ° C. | 120.0 | 225.0 | 120.0 | 225.0 | 57.3 | 138.0 |
| Pressure | kPa | 2550 | 2550 | 1900 | 2550 | 2000 | 1900 |
| Molar Flow | kgmole/h | 132800 | 108949 | 16.02451 | 171.1897 | 411.8927 | 567.0579 |
| Mass Flow | kg/h | 1751214 | 1693600 | 665.4682 | 57607.56 | 70142.66 | 127084.7 |
| Component | | | | Mole fraction | | | |
| Methane | | 0.0084 | 0.0181 | 0.0167 | 0.0016 | 0.0000 | 0.0000 |
| Ethane | | 0.0000 | 0.0018 | 0.0031 | 0.0003 | 0.0000 | 0.0000 |
| Propane | | 0.0000 | 0.0014 | 0.0039 | 0.0004 | 0.0000 | 0.0000 |
| n-Butane | | 0.0000 | 0.0010 | 0.1390 | 0.0005 | 0.0052 | 0.0000 |
| CO | | 0.2987 | 0.2549 | 0.1537 | 0.0144 | 0.0000 | 0.0000 |
| CO2 | | 0.0572 | 0.0703 | 0.0918 | 0.0086 | 0.0000 | 0.0000 |
| Hydrogen | | 0.5973 | 0.4929 | 0.2333 | 0.0218 | 0.0000 | 0.0000 |
| H2O | | 0.0128 | 0.1237 | 0.0000 | 0.0183 | 0.0027 | 0.0075 |
| Nitrogen | | 0.0245 | 0.0298 | 0.0180 | 0.0017 | 0.0000 | 0.0000 |
| Argon | | 0.0010 | 0.0012 | 0.0009 | 0.0001 | 0.0000 | 0.0000 |
| n-Pentane | | 0.0000 | 0.0006 | 0.2738 | 0.0004 | 0.0105 | 0.0000 |
| n-Hexane | | 0.0000 | 0.0004 | 0.0000 | 0.0004 | 0.0273 | 0.0199 |
| n-Heptane | | 0.0000 | 0.0005 | 0.0000 | 0.0010 | 0.0828 | 0.0605 |
| n-Octane | | 0.0000 | 0.0005 | 0.0000 | 0.0014 | 0.1151 | 0.0840 |
| n-Nonane | | 0.0000 | 0.0004 | 0.0000 | 0.0019 | 0.1089 | 0.0797 |
| n-Decane | | 0.0000 | 0.0004 | 0.0000 | 0.0026 | 0.0979 | 0.0719 |
| nC11-nC15 | | 0.0000 | 0.0013 | 0.0000 | 0.0349 | 0.3354 | 0.2542 |
| nC16-nC20 | | 0.0000 | 0.0006 | 0.0000 | 0.1244 | 0.1596 | 0.1535 |
| nC21-nC25 | | 0.0000 | 0.0002 | 0.0000 | 0.2291 | 0.0439 | 0.1011 |
| nC26-nC30 | | 0.0000 | 0.0000 | 0.0000 | 0.5362 | 0.0080 | 0.1677 |
| Methanol | | 0.0000 | 0.0000 | 0.0105 | 0.0000 | 0.0004 | 0.0000 |
| Ethanol | | 0.0000 | 0.0000 | 0.0133 | 0.0000 | 0.0005 | 0.0000 |
| 1-Propanol | | 0.0000 | 0.0000 | 0.0138 | 0.0000 | 0.0005 | 0.0000 |
| 1-Butanol | | 0.0000 | 0.0000 | 0.0055 | 0.0000 | 0.0002 | 0.0000 |
| 1-Pentanol | | 0.0000 | 0.0000 | 0.0021 | 0.0000 | 0.0001 | 0.0000 |
| 1-Hexanol | | 0.0000 | 0.0000 | 0.0006 | 0.0000 | 0.0000 | 0.0000 |
| 1-Heptanol | | 0.0000 | 0.0000 | 0.0001 | 0.0000 | 0.0000 | 0.0000 |
| Propanal | | 0.0000 | 0.0000 | 0.0089 | 0.0000 | 0.0003 | 0.0000 |
| n-Butanal | | 0.0000 | 0.0000 | 0.0075 | 0.0000 | 0.0003 | 0.0000 |
| n-Pentanal | | 0.0000 | 0.0000 | 0.0037 | 0.0000 | 0.0001 | 0.0000 |

-continued

| | | \multicolumn{6}{c}{Stream Number} |
|---|---|---|---|---|---|---|---|
| | | 28 | 30 | 32 | 34 | 40 | 48 |
| Temperature | °C. | 63.7 | 4.8 | 120.0 | 119.1 | 250.0 | 250.0 |
| Pressure | kPa | 2290 | 2000 | 3500 | 1990 | 4000 | 4000 |
| Molar Flow | kgmole/h | 13445.72 | 95091.41 | 43553.28 | 138644.7 | 138644.7 | 90112.1 |
| Mass Flow | kg/h | 242487.3 | 1380970 | 1041929 | 2422899 | 2422899 | 2232301 |
| Component | | \multicolumn{6}{c}{Mole fraction} |
| Methane | | 0.0000 | 0.0207 | 0.2215 | 0.0838 | 0.0838 | 0.1339 |
| Ethane | | 0.0000 | 0.0021 | 0.0229 | 0.0086 | 0.0086 | 0.0140 |
| Propane | | 0.0000 | 0.0016 | 0.0190 | 0.0071 | 0.0071 | 0.0117 |
| n-Butane | | 0.0000 | 0.0012 | 0.0108 | 0.0042 | 0.0042 | 0.0073 |
| CO | | 0.0000 | 0.2920 | 0.2769 | 0.2873 | 0.2873 | 0.1760 |
| CO2 | | 0.0004 | 0.0805 | 0.0239 | 0.0627 | 0.0627 | 0.0964 |
| Hydrogen | | 0.0000 | 0.5647 | 0.1108 | 0.4221 | 0.4221 | 0.0952 |
| H2O | | 0.9992 | 0.0004 | 0.0004 | 0.0004 | 0.0004 | 0.2660 |
| Nitrogen | | 0.0000 | 0.0342 | 0.2971 | 0.1168 | 0.1168 | 0.1796 |
| Argon | | 0.0000 | 0.0013 | 0.0116 | 0.0046 | 0.0046 | 0.0070 |
| n-Pentane | | 0.0000 | 0.0006 | 0.0043 | 0.0018 | 0.0018 | 0.0034 |
| n-Hexane | | 0.0000 | 0.0003 | 0.0006 | 0.0004 | 0.0004 | 0.0010 |
| n-Heptane | | 0.0000 | 0.0003 | 0.0002 | 0.0003 | 0.0003 | 0.0011 |
| n-Octane | | 0.0000 | 0.0001 | 0.0000 | 0.0001 | 0.0001 | 0.0007 |
| n-Nonane | | 0.0000 | 0.0000 | 0.0000 | 0.0000 | 0.0000 | 0.0006 |
| n-Decane | | 0.0000 | 0.0000 | 0.0000 | 0.0000 | 0.0000 | 0.0010 |
| nC11-nC15 | | 0.0000 | 0.0000 | 0.0000 | 0.0000 | 0.0000 | 0.0032 |
| nC16-nC20 | | 0.0000 | 0.0000 | 0.0000 | 0.0000 | 0.0000 | 0.0013 |
| nC21-nC25 | | 0.0000 | 0.0000 | 0.0000 | 0.0000 | 0.0000 | 0.0003 |
| nC26-nC30 | | 0.0000 | 0.0000 | 0.0000 | 0.0000 | 0.0000 | 0.0001 |
| Methanol | | 0.0002 | 0.0000 | 0.0000 | 0.0000 | 0.0000 | 0.0000 |
| Ethanol | | 0.0001 | 0.0000 | 0.0000 | 0.0000 | 0.0000 | 0.0000 |
| 1-Propanol | | 0.0000 | 0.0000 | 0.0000 | 0.0000 | 0.0000 | 0.0000 |
| 1-Butanol | | 0.0000 | 0.0000 | 0.0000 | 0.0000 | 0.0000 | 0.0000 |
| 1-Pentanol | | 0.0000 | 0.0000 | 0.0000 | 0.0000 | 0.0000 | 0.0000 |
| 1-Hexanol | | 0.0000 | 0.0000 | 0.0000 | 0.0000 | 0.0000 | 0.0000 |
| 1-Heptanol | | 0.0000 | 0.0000 | 0.0000 | 0.0000 | 0.0000 | 0.0000 |
| Propanal | | 0.0000 | 0.0000 | 0.0000 | 0.0000 | 0.0000 | 0.0000 |
| n-Butanal | | 0.0000 | 0.0000 | 0.0000 | 0.0000 | 0.0000 | 0.0000 |
| n-Pentanal | | 0.0000 | 0.0000 | 0.0000 | 0.0000 | 0.0000 | 0.0000 |

| | | \multicolumn{7}{c}{Stream Number} |
|---|---|---|---|---|---|---|---|---|
| | | 46 | 52 | 62 | 54 | 64 | 56 | 60 |
| Temperature | °C. | 250.0 | 57.4 | 68.2 | 174.2 | 120.0 | 120.0 | 110.0 |
| Pressure | kPa | 4000 | 3700 | 3775 | 3700 | 3690 | 3690 | 800 |
| Molar Flow | kgmole/h | 629.2001 | 935.7987 | 23968.91 | 1564.999 | 13055.03 | 52152.37 | 8585.572 |
| Mass Flow | kg/h | 190580.5 | 143825 | 432419.8 | 334405.5 | 331555.4 | 1324501 | 281226.1 |
| Component | | \multicolumn{7}{c}{Mole fraction} |
| Methane | | 0.0181 | 0.0000 | 0.0000 | 0.0073 | 0.1850 | 0.1850 | 0.0000 |
| Ethane | | 0.0033 | 0.0000 | 0.0000 | 0.0013 | 0.0194 | 0.0194 | 0.0000 |
| Propane | | 0.0042 | 0.0000 | 0.0000 | 0.0017 | 0.0162 | 0.0162 | 0.0000 |
| n-Butane | | 0.0040 | 0.0613 | 0.0000 | 0.0383 | 0.0092 | 0.0092 | 0.0000 |
| CO | | 0.0161 | 0.0000 | 0.0000 | 0.0065 | 0.2432 | 0.2432 | 0.0739 |
| CO2 | | 0.0173 | 0.0000 | 0.0009 | 0.0070 | 0.1329 | 0.1329 | 0.6863 |
| Hydrogen | | 0.0074 | 0.0000 | 0.0000 | 0.0030 | 0.1316 | 0.1316 | 0.2399 |
| H2O | | 0.0562 | 0.0032 | 0.9990 | 0.0245 | 0.0004 | 0.0004 | 0.0000 |
| Nitrogen | | 0.0166 | 0.0000 | 0.0000 | 0.0067 | 0.2481 | 0.2481 | 0.0000 |
| Argon | | 0.0008 | 0.0000 | 0.0000 | 0.0003 | 0.0097 | 0.0097 | 0.0000 |
| n-Pentane | | 0.0029 | 0.0835 | 0.0000 | 0.0511 | 0.0036 | 0.0036 | 0.0000 |
| n-Hexane | | 0.0013 | 0.0628 | 0.0000 | 0.0381 | 0.0005 | 0.0005 | 0.0000 |
| n-Heptane | | 0.0021 | 0.0940 | 0.0000 | 0.0570 | 0.0002 | 0.0002 | 0.0000 |
| n-Octane | | 0.0020 | 0.0695 | 0.0000 | 0.0424 | 0.0000 | 0.0000 | 0.0000 |
| n-Nonane | | 0.0023 | 0.0558 | 0.0000 | 0.0343 | 0.0000 | 0.0000 | 0.0000 |
| n-Decane | | 0.0057 | 0.0923 | 0.0000 | 0.0575 | 0.0000 | 0.0000 | 0.0000 |
| n-C11-nC15 | | 0.0590 | 0.3066 | 0.0000 | 0.2070 | 0.0000 | 0.0000 | 0.0000 |
| nC16-nC20 | | 0.1361 | 0.1292 | 0.0000 | 0.1320 | 0.0000 | 0.0000 | 0.0000 |
| nC21-nC25 | | 0.1746 | 0.0325 | 0.0000 | 0.0896 | 0.0000 | 0.0000 | 0.0000 |
| nC26-nC30 | | 0.4696 | 0.0084 | 0.0000 | 0.1939 | 0.0000 | 0.0000 | 0.0000 |
| Methanol | | 0.0000 | 0.0001 | 0.0000 | 0.0001 | 0.0000 | 0.0000 | 0.0000 |
| Ethanol | | 0.0000 | 0.0001 | 0.0000 | 0.0001 | 0.0000 | 0.0000 | 0.0000 |
| 1-Propanol | | 0.0000 | 0.0001 | 0.0000 | 0.0000 | 0.0000 | 0.0000 | 0.0000 |
| 1-Butanol | | 0.0000 | 0.0000 | 0.0000 | 0.0000 | 0.0000 | 0.0000 | 0.0000 |
| 1-Pentanol | | 0.0000 | 0.0000 | 0.0000 | 0.0000 | 0.0000 | 0.0000 | 0.0000 |
| 1-Hexanol | | 0.0000 | 0.0000 | 0.0000 | 0.0000 | 0.0000 | 0.0000 | 0.0000 |

-continued

| | | | | | | | |
|---|---|---|---|---|---|---|---|
| 1-Heptanol | 0.0000 | 0.0000 | 0.0000 | 0.0000 | 0.0000 | 0.0000 | 0.0000 |
| Propanal | 0.0000 | 0.0005 | 0.0000 | 0.0003 | 0.0000 | 0.0000 | 0.0000 |
| n-Butanal | 0.0000 | 0.0002 | 0.0000 | 0.0001 | 0.0000 | 0.0000 | 0.0000 |
| n-Pentanal | 0.0000 | 0.0000 | 0.0000 | 0.0000 | 0.0000 | 0.0000 | 0.0000 |

The present invention, utilizing the Ru catalyst in this way is able to provide a selectivity to C5+ hydrocarbons of 95% or higher, plus a heavier wax distribution, than the conventional cobalt catalyst-based processes, which currently offer at best C5+ selectivities in the range 86-88%. Accordingly, the process of the present invention offers considerable increases in productivity that offset the potential increased cost of using a precious metal catalyst.

The invention claimed is:

1. A process for the conversion of synthesis gas into hydrocarbons comprising the steps of;
   (i) passing a synthesis gas comprising hydrogen and carbon monoxide over a cobalt catalyst at a temperature in the range 210-225° C. to produce a first reaction product mixture comprising hydrocarbons, steam, carbon monoxide and hydrogen of a first reaction stage,
   (ii) condensing and separating water from the first reaction product mixture to produce a de-watered first reaction product mixture,
   (iii) passing the de-watered first reaction product mixture over a supported ruthenium catalyst at a temperature in the range 230-265° C. and a pressure in the range 35-55 bar abs, to produce a second reaction product mixture containing hydrocarbons of a second reaction stage, and
   (iv) recovering the hydrocarbons from the second reaction product mixture
   wherein the pressure of the second reaction stage is higher than that of the first reaction stage, and the pressure of the first reactor stage is at least 5 bar abs.

2. A process according to claim 1, wherein the cobalt catalyst comprises cobalt supported on an oxidic support or silicon carbide support.

3. A process according to claim 2, wherein the oxidic support is selected from the group consisting of alumina, silica, titanic, zirconia, zinc oxide, and a mixture thereof.

4. A process according to claim 2, wherein the oxidic support is selected from the group consisting of alpha alumina, a transition alumina, a hydrated alumina, an alpha alumina coated in a layer of metal aluminate, and a transition alumina coated in a layer of metal aluminate.

5. A process according to claim 1, wherein the cobalt catalyst comprises an intimate mixture of cobalt and oxidic compounds.

6. A process according to claim 5, wherein the oxidic compounds comprise cobalt-aluminium oxide or cobalt-zinc oxide compounds.

7. A process according to claim 1, wherein the cobalt catalyst is free of precious metal promoters.

8. A process according to claim 1, wherein the cobalt content of the cobalt catalyst is in the range 5-45% by weight.

9. A process according to claim 1, wherein the cobalt catalyst is in a form selected from the group consisting of a powder with a volume-median diameter in the range 1 to 200 micrometers, a shaped unit with a particle size in the range 1-25 mm, and a coating on a metal or ceramic support.

10. A process according to claim 1, wherein the ruthenium catalyst comprises ruthenium supported on an oxidic support, graphite, or silicon carbide support.

11. A process according to claim 10, wherein the oxidic support is selected from the group consisting of alumina, silica, titanic, zirconia, zinc oxide, and a mixture thereof.

12. A process according to claim 10, wherein the oxidic support is selected from the group consisting of an alpha alumina, a transition alumina, a hydrated alumina, and an alumina coated in a layer of metal aluminate.

13. A process according to claim 1, wherein the ruthenium catalyst is free of cobalt.

14. A process according to claim 1, wherein the ruthenium content of the ruthenium catalyst is in the range 0.1-10% by weight.

15. A process according to claim 1, wherein the ruthenium catalyst is a powder with a volume-median diameter in the range 1 to 200 micrometers, a shaped unit with a particle size in the range 1-25 mm, and a coating on a metal or ceramic support.

16. A process according to claim 1, wherein the first reaction stage is performed by passing the synthesis gas mixture through a fixed bed of the cobalt catalyst or through a slurry of the cobalt catalyst in a hydrocarbon liquid medium.

17. A process according to claim 1, wherein the second reaction stage is performed by passing the synthesis gas mixture through a fixed bed of the ruthenium catalyst or through a slurry of the ruthenium catalyst in a hydrocarbon liquid medium.

18. A process according to claim 1, wherein the temperature of the first reaction product mixture is adjusted by heat exchange before the second reaction stage.

19. A process according to claim 1, wherein the composition of the first stage reaction mixture is adjusted by addition of synthesis gas, hydrogen, carbon monoxide, or an inert gas or by the removal of hydrocarbon or steam.

20. A process according to claim 1, wherein >50% of the conversion of the synthesis gas occurs over the ruthenium catalyst.

21. A process according claim 1, operated under conditions such that the conversion of the synthesis gas to hydrocarbons in the second stage reaction mixture is ≥90% on a molar basis.

22. A process according to claim 1, wherein the recovery of hydrocarbons from the second stage reaction product mixture creates a tail gas comprising hydrogen, carbon monoxide, carbon dioxide, and methane, and at least a portion of the tail gas is recycled to one or more of an upstream synthesis gas generation stage, the synthesis gas fed to the cobalt catalyst, the first stage reaction product mixture fed to the ruthenium catalyst, or a separation stage that provides one or more gases enriched in hydrogen, carbon monoxide, carbon dioxide, or methane.

23. A process according to claim 22, wherein at least a portion of the tail gas is recycled to the ruthenium-catalysed stage.

24. A process according to claim 22, wherein at least a portion of one or more of the gasses recovered in the separation stage is recycled to one or more of an upstream synthesis gas generation stage, the synthesis gas fed to the cobalt catalyst, the first stage reaction product mixture fed to the ruthenium catalyst, or a downstream hydrocarbon processing stage.

25. A process according to claim 24, wherein $CO_2$ formed in the first and second stage reaction is recovered from the tail gas.

26. A process according to claim 1, wherein the recovery of hydrocarbons from the first or second stage reaction product mixture creates a co-produced water stream comprising water and oxygenated hydrocarbons and at least a portion of the co-produced water is recycled to an upstream synthesis gas generation stage or a separation stage that provides a stream enriched in oxygenates.

27. A process according to claim 26, wherein at least a portion of the oxygenates from the separation stage is recycled to an upstream synthesis gas generation stage.

* * * * *